United States Patent
Horlacher et al.

(10) Patent No.: US 7,179,929 B2
(45) Date of Patent: Feb. 20, 2007

(54) METHOD FOR PRODUCING CONJUGATED LINOLEIC ACID GLYCERIDES

(75) Inventors: Peter Horlacher, Bellenberg (DE); Franz Timmermann, Illertissen (DE); Juergen Gierke, Illertissen/Betlinshausen (DE); Karl-Heinz Ruf, Babenhausen (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 53 days.

(21) Appl. No.: 10/513,314

(22) PCT Filed: Apr. 25, 2003

(86) PCT No.: PCT/EP03/04302

§ 371 (c)(1),
(2), (4) Date: Nov. 3, 2004

(87) PCT Pub. No.: WO03/093214

PCT Pub. Date: Nov. 13, 2003

(65) Prior Publication Data

US 2005/0176977 A1    Aug. 11, 2005

(30) Foreign Application Priority Data

May 3, 2002   (DE) ............................... 102 19 781

(51) Int. Cl.
*C07C 51/00*   (2006.01)

(52) U.S. Cl. ..................................................... 554/124
(58) Field of Classification Search ................. 554/124
See application file for complete search history.

(56) References Cited

U.S. PATENT DOCUMENTS

| 3,162,658 A | 12/1964 | Wechmann et al. |
| 6,177,580 B1 | 1/2001 | Timmermann et al. |
| 2001/0025113 A1 | 9/2001 | Ageir et al. |

FOREIGN PATENT DOCUMENTS

| DE | 197 18 245 C1 | 7/1998 |
| WO | WO 03/022964 A1 | 3/2003 |

*Primary Examiner*—Deborah D. Carr
(74) *Attorney, Agent, or Firm*—John F. Daniels

(57) ABSTRACT

Processes for preparing conjugated fatty acid glycerides comprising: (a) isomerizing a fatty acid lower alkyl ester corresponding to the general formula (I) in the presence of a basic catalyst at a temperature of from 100 to 160° C., to form a conjugated fatty acid lower alkyl ester:

$$R^1CO-OR^2 \qquad (I)$$

wherein $R^1CO$ represents an acyl radical having from 16 to 22 carbon atoms and at least two carbon-carbon unsaturations and $R^2$ represents an alkyl radical having from 1 to 4 carbon atoms; and (b) transesterifying the conjugated fatty acid lower alkyl ester with glycerol to form a conjugated fatty acid glyceride, wherein a lower alkanol corresponding to the general formula $R^2OH$ is formed, wherein $R^2$ is as defined above, and the lower alkanol is continuously removed from the transesterification reaction; are described.

20 Claims, No Drawings

METHOD FOR PRODUCING CONJUGATED LINOLEIC ACID GLYCERIDES

This application is a 371 of PCT/EP03/04302 filed Apr. 25, 2003.

TITLE OF THE INVENTION

Processes for Preparing Conjugated Fatty Acid Glycerides

BACKGROUND OF THE INVENTION

Linoleic acid having conjugated double bonds, which are on the market under the name "CLA" (conjugated linoleic acid), are physiologically active and are used as food additives. A disadvantage is that they are highly hydrophilic and are therefore only incorporated into oil phases or absorbed by fats with difficulty. In addition, they can undergo unwanted reactions with other food constituents, which leads to sensory disadvantages (taste, odor, coloration) and is therefore undesirable. The problem can be avoided if, instead of the free acids, the corresponding triglycerides are used. According to the methods of the prior art, as represented, for example, by German patent DE 19718245 C2 (Cognis), although these conjugated linoleic acid glycerides can be synthesized in principle, it is a disadvantage that they have a comparatively high content of physiologically inactive and unwanted trans, trans-double-bond isomers.

It is therefore an object of the present invention to develop an improved method of preparing conjugated linoleic acid glycerides which is successful with very low equipment requirements and secondly provides products which are distinguished by a very low content of trans, trans-double-bond isomers and a very high content of c9,t11- and t10, c12-isomers.

BRIEF SUMMARY OF THE INVENTION

The present invention relates, in general, to food additives and relates to an improved one-pot method of preparing conjugated fatty acid glycerides, especially specific conjugated linoleic acid glycerides.

The invention relates to a method for preparing conjugated linoleic acid glycerides having a reduced content of trans, trans-isomers which comprises
(a) subjecting fatty acid low-alkyl esters of the formula (I), $$R^1CO—OR^2 \quad (I)$$

where $R^1CO$ is a predominantly polyunsaturated acyl radical having 16 to 22, preferably 18 to 20, carbon atoms and $R^2$ is an alkyl radical having 1 to 4 carbon atoms and is preferably methyl, to a double-bond isomerization using basic catalysts at temperatures in the range from 100 to 160° C., and
(b) transesterifying the resultant conjuene fatty acid low-alkyl esters with glycerol to give the corresponding glycerides and continuously distilling off the lower alcohol released.

Surprisingly, it has been found that the desired conjugated linoleic acid glycerides having a content, based on the content of conjugated linoleic acid, of trans/trans double-bond isomers of less than 3% by weight, and a content, based on the content of conjugated linoleic acid, of c9, t11- and t10, c12-double-bond isomers of, together, at least 95% by weight can be prepared in a simple one-pot reaction, where, in the first step, an alkali-metal-catalyzed double-bond isomerization is carried out and then, without addition of further catalyst and under constant reaction conditions, transesterification with addition of glycerol is carried out.

DETAILED DESCRIPTION OF THE INVENTION

Starting Materials

Starting materials preferably used for preparing the conjugated linoleic acid glycerides are fatty acid low-alkyl esters which have a content of diunsaturated and/or triunsaturated acyl radicals of more than 50, and in particular more than 60, mol %, for example sunflower fatty acid, safflower fatty acid or rapeseed fatty acid alkyl esters. Usually, methyl or ethyl esters are used as starting material.

Double-Bond Isomerization

For isomerization of the isolated double bonds in the starting esters, that is to say for forming the conjuene fatty acid esters, generally basic catalysts of the type of alkaline metal hydroxides or alkali metal alkoxides are used, in particular anhydrous or in alcoholic solution. The amount used can be from 1 to 5% by weight, based on the ester used. Typical reaction times are in the range from 1 to 6 h, preferably from 2 to 4 h, and temperatures from 100 to 160° C., preferably from 120 to 140° C.

Transesterification and Work-Up

One of the essential advantages of the method is that it is a one-pot reaction, that is to say the conjuene fatty acid esters formed as intermediates need not be isolated, but can be directly transesterified to glyceride with addition of glycerol. Generally, it is not even necessary to add further catalyst. Usually, fatty acid low-alkyl esters and glycerol are used in a molar ratio of 1:0.3 to 1:0.5, the amount usually being chosen such that it is sufficient to form a random mono-/di-/triester mixture. The transesterification can be carried out at temperatures in the range from 100 to 160° C., preferably from 120 to 140° C., if appropriate under a reduced pressure from 50 to 100 mbar. The alcohol released in the method is continuously removed from the reaction equilibrium in order to contribute to product formation. The catalyst is then neutralized by adding a mineral acid, for example phosphoric acid, or an organic acid, for example lactic acid and filtered with addition of filter aids, in order to obtain a clear product. If desired, the glyceride can then be deodorized in a thin-film evaporator.

EXAMPLES

Example 1

200 g of sunflower fatty acid methyl ester were charged together with 6.4 g of potassium methoxide into a 500 ml 3-neck flask equipped with stirrer, dropping funnel and reflux condenser and heated in the course of 2 h to 130° C. and held at this temperature for 1.5 h. 48.1 g of glycerol were then added dropwise, the mixture was further stirred at 130° C. for 1 h and the pressure was then reduced to 80 mbar. After a further stirring time of 2 h at 130° C., the batch was cooled to 75° C., aerated with nitrogen and neutralized by adding phosphoric acid, in which case brightening of the color was observed. A filter aid was then added to the product which was filtered through a Beco C1 filter plate and deodorized using a thin-film evaporator. The reaction product composition is shown in Table 1.

TABLE 1

Reaction product composition

| Composition | % by weight |
|---|---|
| Total content of conjugated linoleic acid | 61.0 |
| c9, t11 isomer | 30.0 |
| t10, c12 isomer | 29.4 |
| c, c isomers | 0.9 |
| t, t isomers | 0.9 |

Example 2

200 g of safflower fatty acid methyl ester were placed together with 4.4 g of potassium tert-butyl oxide in a 500 ml 3-neck flask equipped with stirrer, dropping funnel and reflux condenser and heated in the course of 2 h to 130° C. and kept at this temperature for 1.5 h. 48.1 g of glycerol was then added dropwise, the mixture was further stirred at 130° C. for 1 h and the pressure was then reduced to 80 mbar. After a further stirring time of 2 h at 130° C., the batch was cooled to 75° C., aerated with nitrogen and neutralized by adding phosphoric acid, in which case a brightening of the color was observed. A filter aid was then added to the product, the mixture was filtered through a Beco C1 filter plate and deodorized using a thin-film evaporator. The reaction product composition is shown in Table 2.

TABLE 2

Reaction product composition

| Composition | % by weight |
|---|---|
| Total content of conjugated linoleic acid | 74.0 |
| c9, t11 isomer | 36.0 |
| t10, c12 isomer | 35.0 |
| c, c isomers | 1.4 |
| t, t isomers | 1.2 |

Comparative Example V1

320 g of fatty acid (conjugated linoleic acid: 76%, of which c9, t11: 35.5% and t10,c12: 36.2%) and 35 g of glycerol were placed together with 0.25 g of tin (II) oxalate, 4.4 g of potassium methoxide in a 500 ml 3-neck flask equipped with stirrer, dropping funnel and reflux condenser and heated in the course of 2 h to 210° C. and kept at this temperature under a pressure of 800 mbar for 2 h. The pressure was then reduced to <30 mbar. The batch was cooled to 75° C., aerated with nitrogen and neutralized by adding phosphoric acid. A filter aid was then added to the product, the mixture was filtered through a Beco C1 filter plate and deodorized using a thin-film evaporator. The reaction product composition is shown in Table 3.

TABLE 3

Reaction product composition

| Composition | % by weight |
|---|---|
| Total content of conjugated linoleic acid | 76.0 |
| c9, t11 isomer | 30.3 |
| t10, c12 isomer | 28.5 |
| c, c isomers | 5.7 |
| t, t isomers | 11.1 |

What is claimed is:

1. A process comprising:
   (a) isomerizing a fatty acid lower alkyl ester corresponding to the general formula (I) in the presence of a basic catalyst at a temperature of from 100 to 160° C., to form a conjugated fatty acid lower alkyl ester:

$$R^1CO\text{---}OR^2 \qquad (I)$$

wherein $R^1CO$ represents an acyl radical having from 16 to 22 carbon atoms and at least two carbon-carbon unsaturations and $R^2$ represents an alkyl radical having from 1 to 4 carbon atoms; and
   (b) transesterifying the conjugated fatty acid lower alkyl ester with glycerol to form a conjugated fatty acid glyceride, wherein a lower alkanol corresponding to the general formula $R^2OH$ is formed, wherein $R^2$ is as defined above, and the lower alkanol is continuously removed from the transesterification reaction.

2. The process according to claim 1, wherein the fatty acid lower alkyl ester comprises a mixture of fatty acid lower alkyl esters corresponding to the general formula (I), wherein a predominant portion of the mixture is comprised of fatty acid lower alkyl esters corresponding to the general formula (I) wherein $R^1CO$ represents an acyl radical having from 16 to 22 carbon atoms and at least two carbon-carbon unsaturations.

3. The process according to claim 2, wherein at least 50 mole % of the mixture is comprised of fatty acid lower alkyl esters corresponding to the general formula (I) wherein $R^1CO$ represents an acyl radical having from 16 to 22 carbon atoms and at least two carbon-carbon unsaturations.

4. The process according to claim 2, wherein at least 60 mole % of the mixture is comprised of fatty acid lower alkyl esters corresponding to the general formula (I) wherein $R^1CO$ represents an acyl radical having from 16 to 22 carbon atoms and at least two carbon-carbon unsaturations.

5. The process according to claim 2, wherein the mixture of fatty acid lower alkyl esters comprises a component selected from the group consisting of sunflower fatty acid esters, safflower fatty acid esters, rapeseed fatty acid esters and mixtures thereof.

6. The process according to claim 2, wherein the mixture of fatty acid lower alkyl esters comprises safflower fatty acid esters.

7. The process according to claim 1, wherein $R^2$ represents an alkyl radical having from 1 to 2 carbon atoms.

8. The process according to claim 2, wherein the mixture of fatty acid lower alkyl esters comprises methyl or ethyl esters.

9. The process according to claim 3, wherein the mixture of fatty acid lower alkyl esters comprises methyl or ethyl esters.

10. The process according to claim 6, wherein the mixture of fatty acid lower alkyl esters comprises methyl or ethyl esters.

11. The process according to claim 1, wherein the basic catalyst comprises a basic component selected from the group consisting of alkali metal hydroxides, alkali metal alkoxides and mixtures thereof.

12. The process according to claim 2, wherein the basic catalyst comprises a basic component selected from the group consisting of alkali metal hydroxides, alkali metal alkoxides and mixtures thereof.

13. The process according to claim 3, wherein the basic catalyst comprises a basic component selected from the group consisting of alkali metal hydroxides, alkali metal alkoxides and mixtures thereof.

14. The process according to claim 5, wherein the basic catalyst comprises a basic component selected from the group consisting of alkali metal hydroxides, alkali metal alkoxides and mixtures thereof.

15. The process according to claim 1, wherein the isomerization is carried out over a period of from 1 to 6 hours.

16. The process according to claim 1, wherein the conjugated fatty acid lower alkyl ester and the glycerol are reacted in a molar ratio of from 1:0.3 to 1:0.5.

17. The process according to claim 1, wherein the transesterification reaction is carried out at temperatures of from 100 to 160° C.

18. The process according to claim 2, wherein the mixture of fatty acid lower alkyl esters is isomerized to form a mixture of conjugated fatty acid lower alkyl esters, and the mixture of conjugated fatty acid lower alkyl esters is transesterified with glycerol to form a mixture of conjugated fatty acid glycerides, wherein the mixture of conjugated fatty acid glycerides contains less than 3% by weight of conjugated linoleic acid moieties having trans-trans double bonds, based on the total content of conjugated linoleic acid moieties.

19. The process according to claim 2, wherein the mixture of fatty acid lower alkyl esters is isomerized to form a mixture of conjugated fatty acid lower alkyl esters, and the mixture of conjugated fatty acid lower alkyl esters is transesterified with glycerol to form a mixture of conjugated fatty acid glycerides, wherein the mixture of conjugated fatty acid glycerides contains at least 95% by weight of c9,t11- and t10,c12-isomers of conjugated linoleic acid moieties, based on the total content of conjugated linoleic acid moieties.

20. A process comprising:
(a) isomerizing a mixture of fatty acid lower alkyl esters corresponding to the general formula (I) to form a conjugated fatty acid methyl ester, in the presence of a basic catalyst comprising a basic component selected from the group consisting of alkali metal hydroxides, alkali metal alkoxides and mixtures thereof at a temperature of from 100 to 160° C.:

$$R^1CO\text{---}OR^2 \qquad (I)$$

wherein a predominant portion of the mixture is comprised of fatty acid methyl esters corresponding to the general formula (I) wherein $R^1CO$ represents an acyl radical having from 16 to 22 carbon atoms and at least two carbon-carbon unsaturations; and (b) transesterifying the conjugated fatty acid methyl ester with glycerol to form a conjugated fatty acid glyceride, wherein methanol is formed, and the methanol is continuously removed from the transesterification reaction.

* * * * *